United States Patent [19]

Nustad

[11] Patent Number: 5,610,509
[45] Date of Patent: Mar. 11, 1997

[54] METHOD FOR OPTIMIZING POWER SUPPLY VOLTAGE TO HIGH VOLTAGE TRANSMITTERS

[75] Inventor: Timothy A. Nustad, Greenfield, Wis.

[73] Assignee: General Electric Company, Milwaukee, Wis.

[21] Appl. No.: 343,077

[22] Filed: Nov. 21, 1994

[51] Int. Cl.$^6$ ........................................ A61B 8/02
[52] U.S. Cl. ................... 323/234; 128/661.02; 323/911
[58] Field of Search ..................... 323/234, 911; 128/660.01, 661.02, 661.07

[56] References Cited

U.S. PATENT DOCUMENTS

| | | | |
|---|---|---|---|
| 5,022,406 | 6/1991 | Tomlinson | 128/719 |
| 5,156,157 | 10/1992 | Valenta, Jr. et al. | 128/662.06 |
| 5,188,106 | 2/1993 | Nappholz et al. | 128/419 PG |
| 5,287,111 | 2/1994 | Shpater | 342/28 |

*Primary Examiner*—Mathew V. Nguyen
*Attorney, Agent, or Firm*—B. Joan Haushalter; John H. Pilarski

[57] ABSTRACT

A transmit power supply optimization method optimizes power supply voltage to high voltage transmitters of an ultrasound imaging apparatus for each operating mode of the apparatus. The method comprises the steps of linking the operating mode of the apparatus, the output of the high voltage transmitters, and the power supply. It is then determined when a change in optimum power supply voltage will be desired. Operation of the high voltage transmitter power supply and the high voltage transmitters is coordinated to react to the determination that a change in optimum power supply voltage will be desired, before the change in optimum power supply voltage is actually desired. Finally, a distributed power supply filter is provided to allow the high voltage transmitters to operate while the change in optimum power supply voltage is occurring.

4 Claims, 1 Drawing Sheet

METHOD FOR OPTIMIZING POWER SUPPLY VOLTAGE TO HIGH VOLTAGE TRANSMITTERS

TECHNICAL FIELD

The present invention relates to ultrasound imaging and, more particularly, to optimization of the transmit power supply in ultrasound imaging apparatus.

BACKGROUND ART

During the operation of a medical ultrasound instrument, the efficiency of the high voltage transmitters can be optimized by setting the supply voltage of the transmitters to the minimum level required for the transmitters to operate. This supply optimization reduces the power consumed by the instrument and reduces the heat generated by the power supply and transmitters.

The optimum power supply voltage for the transmitters will depend upon the particular mode (i.e. B-mode, doppler, color flow, or continuous wave) in which the ultrasound machine is operating. The operating mode may change very rapidly, and optimum supply voltage can change at millisecond rates as the operating modes are intermixed.

In situations where the operating mode is changing rapidly, previous power supplies have not been able to change output voltage rapidly enough to track the mode changes without introducing lengthy delays at each mode change. In order to eliminate these delays when intermixing modes, the supply must be set to provide adequate voltage for the worst case mode. The other modes in the operating sequence then operate at higher than optimal voltage levels, reducing electrical efficiency and creating excess heat.

It would be desirable then to have a means for optimizing the power supply voltage to the high voltage transmitters for each operating mode, even when the modes are rapidly intermixed.

SUMMARY OF THE INVENTION

The present invention allows the power supply voltage to the high voltage transmitters to be optimized for each operating mode, even when the modes are rapidly intermixed. This architecture also allows the ultrasound machine to image while the power supply is changing modes as a means to eliminate delays when mixing modes.

In accordance with one aspect of the present invention, a transmit power supply optimization method optimizes power supply voltage to high voltage transmitters of an ultrasound imaging apparatus for each operating mode of the apparatus. The method comprises the steps of linking the operating mode of the apparatus, the output of the high voltage transmitters, and the power supply. It is then determined when a change in optimum power supply voltage will be desired. Operation of the high voltage transmitter power supply and the high voltage transmitters is coordinated to react to the determination that a change in optimum power supply voltage will be desired, before the change in optimum power supply voltage is actually desired. Finally, a distributed power supply filter is provided to allow the high voltage transmitters to operate while the change in optimum power supply voltage is occurring.

Accordingly, it is an object of the present invention to allow the power supply voltage to the high voltage transmitters to be optimized for each operating mode. It is a further object of the present invention to allow the power supply voltage to the high voltage transmitters to be optimized for each operating mode, even when the modes are rapidly intermixed. It is also an object of the present invention to allow the ultrasound machine to image while the power supply is changing modes as a means to eliminate delays when mixing modes.

Other objects and advantages of the invention will be apparent from the following description, the accompanying drawings and the appended claims.

DETAILED DESCRIPTION OF THE PREFERRED EMBODIMENTS

The present invention is particularly adaptable for use on a medical ultrasound machine. The present invention provides a power supply control and distribution architecture that allows the power supply voltage to the high voltage transmitters to be optimized for each operating mode, even when the modes are rapidly intermixed. This architecture, illustrated in FIG. 1, also allows the ultrasound machine to image while the power supply is changing modes, as a means for eliminating delays when mixing modes.

Figure 1:
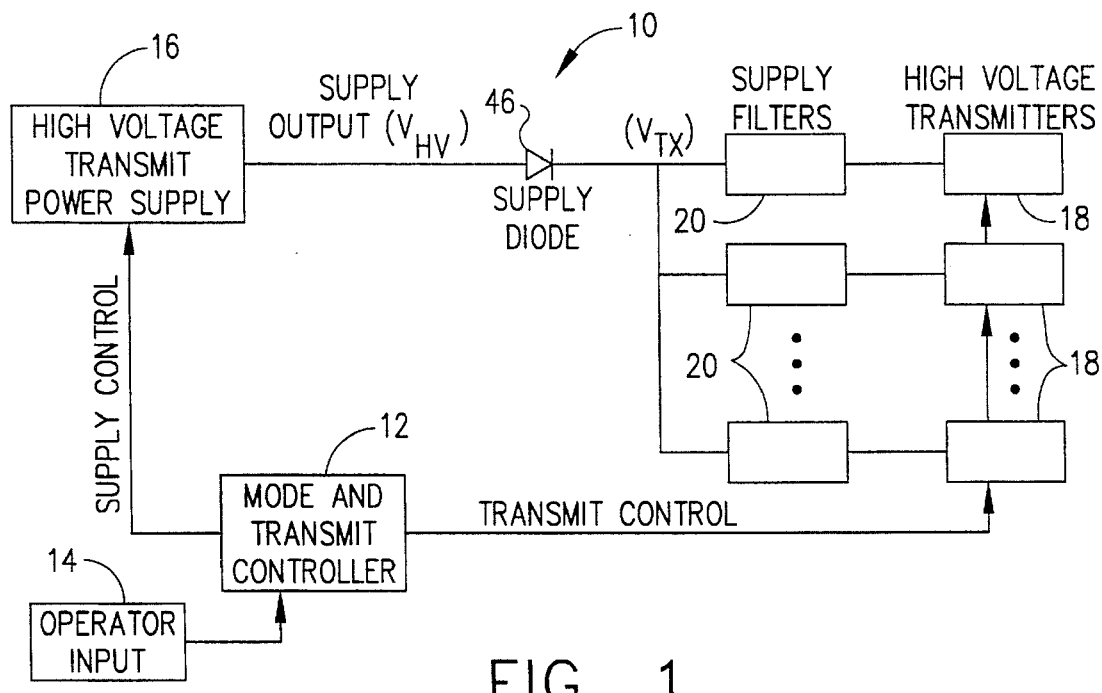
FIG. 1 is a block diagram of the transmit power supply and control distribution according to the present invention.

Referring now to FIG. 1, there is illustrated a block diagram of a transmit power supply and control distribution system 10, according to the present invention. During operation, mode and transmit controller 12 processes operator inputs from block 14 to optimize power supply voltage from high voltage transmit power supply 16. The power supply voltage is optimized for the most efficient operation of high voltage transmitters 18 in a current scanning mode.

The present invention provides a means for eliminating delays created by waiting for the power supply 16 to increase the transmitter supply voltage magnitude ($V_{TX}$). This is accomplished by allowing the controller 12 to anticipate an increase in magnitude, and thereby begin increasing the magnitude of the supply output ($V_{HV}$) prior to the time at which the mode change takes place, as illustrated in FIG. 2.

Figure 2:
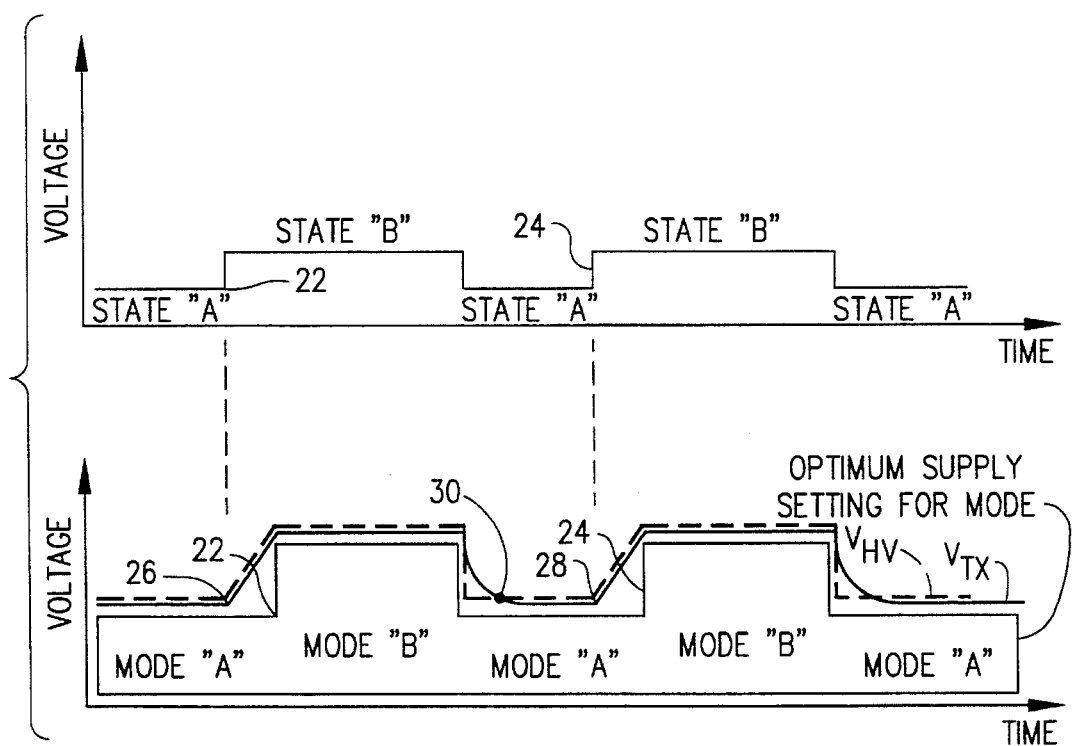
FIG. 2 illustrates graphical representations of the supply control and operating voltages during mixed mode operation.

The top portion of FIG. 2 illustrates the points in time, i.e., points 22 and 24, when the supply output is required to increase from state "A" to state "B". The lower portion of FIG. 2 illustrates the increase in magnitude of the supply output (with the increase beginning at points 26 and 28, so the desired magnitude is achieved by the point in time indicated by points 22 and 24) prior to the time at which the mode change takes place. The increase in magnitude from state "A" to state "B" is anticipated, so that the desired supply voltage magnitude is achieved at the point in time it is required, instead of beginning the increase in supply voltage magnitude at the point in time at which the increase is required. This allows the supply voltage magnitude at the transmitters 18 to increase to the proper value required before transmit begins for the new mode. Associated supply filters 20 allow each transmitter 18 to operate without interference as $V_{TX}$ is changing.

In the case where the optimization requires the magnitude of the supply voltage to be reduced, the supply output ($V_{HV}$) is reduced at the time of the mode change. If a decrease were anticipated, and the voltage lowered in anticipation of the level needed by state "A" (i.e., prior to the conclusion of state "B"), there would not be enough voltage supplied at the end of state "B". Hence, the supply output is reduced at the time of the mode change, when the magnitude of the supply voltage is to be reduced. The transmitters 18 then begin operating off of the excess charge in the supply filters 20. When this excess charge is depleted, as indicated by point 30, and $V_{TX}$ approaches $V_{HV}$, supply diode 46 will begin to conduct and the high voltage power supply 16 will resume sourcing current to the transmitters 18. This supply diode arrangement further improves efficiency by eliminating the need for the power supply 16 to sink current when the magnitude of $V_{TX}$ is greater than the magnitude of the optimized supply voltage appearing at $V_{HV}$.

FIG. 2 illustrates the relationship between the optimum power supply value at the transmitters ($V_{TX}$), the voltage at the supply output ($V_{HV}$), and the power supply control signal for a typical mixed mode operating sequence. The transmitters 18 are allowed to operate continuously and are not disabled during the power supply transitions.

The invention has been described in detail with particular reference to certain preferred embodiments thereof, but it will be understood that modifications and variations can be effected within the spirit and scope of the invention.

I claim:

1. A method for optimizing power supply voltage to high voltage transmitters of an ultrasound imaging apparatus for each operating mode of the apparatus, the high voltage transmitters having an output, the method comprising the steps of:

linking the operating mode of the apparatus, the output of the high voltage transmitters, and the high voltage transmitter power supply;

determining when a change in optimum power supply voltage will be desired;

differentiating between an anticipated increase in optimum power supply voltage and an anticipated decrease in optimum power supply voltage; and coordinating operation of the high voltage transmitter power supply and the high voltage transmitters to react to the determination that an increase in optimum power supply voltage will be desired, before the change in optimum power supply voltage is actually desired.

2. A method for optimizing power supply voltage to high voltage transmitters of an ultrasound imaging apparatus for each operating mode of the apparatus as claimed in claim 1 further comprising the step of providing a distributed power supply filter to allow the high voltage transmitters to operate while the change in optimum power supply voltage is occurring.

3. A method for optimizing power supply voltage to high voltage transmitters of an ultrasound imaging apparatus for each operating mode of the apparatus as claimed in claim 1 further comprising the step of reacting to the determination that a decrease in optimum power supply voltage is required when the change in optimum power supply voltage is actually desired.

4. A method for optimizing power supply voltage to high voltage transmitters of an ultrasound imaging apparatus for each operating mode of the apparatus as claimed in claim 1 further comprising the step of providing a supply diode to further improve operating efficiency when it is desired to decrease the magnitude of optimum voltage of the transmitter.

* * * * *